United States Patent [19]

Schmidbaur et al.

[11] 4,083,875
[45] Apr. 11, 1978

[54] TRIMETHYL PHOSPHINIMINO DIMETHYL METHYLENE PHOSPHORANE AND PROCESS FOR MAKING IT

[75] Inventors: Hubert Schmidbaur, Garching; Hans-Jürgen Füller, Unterpfaffenhofen, both of Germany

[73] Assignee: Hoechst Aktiengesellschaft, Frankfurt am Main, Germany

[21] Appl. No.: 750,586

[22] Filed: Dec. 15, 1976

[30] Foreign Application Priority Data

Dec. 20, 1975 Germany .................. 2557611

[51] Int. Cl.² .................................. C07F 9/50
[52] U.S. Cl. .................... 260/606.5 P; 260/429 R; 260/606.5 F
[58] Field of Search .................. 260/606.5 P

[56] References Cited

U.S. PATENT DOCUMENTS 3,414,564  12/1968  Krubiner et al. ......... 260/606.5 P X

OTHER PUBLICATIONS

Hoffmann, Ber. 95 2563–2566 (1962).

Rave, J. Org. Chem. 32 3461–3466 (1967).
Koster et al., Ann. Chem. 739 211–219 (1970).
Schmidbaur et al., Angew. Chem. V79, 413 (1967).
Schmidbaur et al., Ber. 100 1120–1128 (1967).

*Primary Examiner*—Helen M. S. Sneed
*Attorney, Agent, or Firm*—Connolly and Hutz

[57] ABSTRACT

Trimethyl phosphinimino dimethyl methylene phosphorane of the formula:

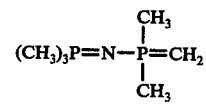

which is a novel chemical compound is produced. To this end, a tetramethyl phosphonium halide is reacted with 1.1 to 1.5 times the molar quantity of an alkali metal amide in an organic solvent, at 0° to 35° C, with the exclusion of air and moisture, and over a period of 24 to 72 hours. The reaction mixture is freed from residue and subjected to fractional distillation.

4 Claims, No Drawings

TRIMETHYL PHOSPHINIMINO DIMETHYL METHYLENE PHOSPHORANE AND PROCESS FOR MAKING IT

The preparation of trimethyl methylene phosphorane of the formula $(CH_3)_3P=CH_2$ by the dehydrohalogenation of tetramethyl phosphonium halides with approximately equimolar proportions of sodium amide in boiling tetrahydrofurane ($bp_{760}=56°$ C) has already been described (Liebigs Ann. Chem. 739 (1970), pages 211–219). As has been found, this reaction is accompanied by side-reactions and, if the reaction conditions are appropriately modified, it produces trimethyl phosphinimino dimethyl methylene phosphorane (II) in unexpected high yields. During the reaction, ammonia is set free together with methane which could be reliably identified by gas-chromatographic analysis. The reaction may reasonably be assumed to take place as shown by the following reaction equations:

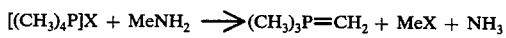

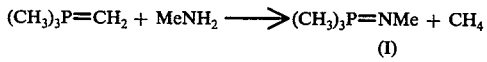

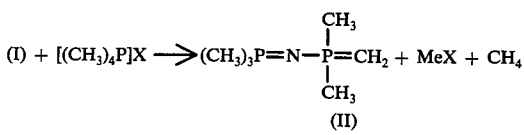

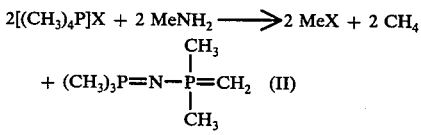

in which X stands for chlorine or bromine, and Me stands for sodium or potassium.

As it would appear, iminotrimethyl phosphorane of formula I is obtained as a by-product, of which the anion being a strong nucleophil is perfectly able to attack a second phosphonium center with the resultant formation of the above formula II compound, while methane is split off. Tests have shown that $(CH_3)_3P=CH_2$ indeed undergoes reaction at 25° C with $NaNH_2$ while methane is set free (cf. equation 2 above).

It is therefore desirable for the synthesis of the above formula II compound to be effected with the use of a molar excess of sodium amide so as to support the reaction of equation 2. By reducing the reaction temperature to less than 35° C, it is also possible owing to the different degrees of solubility of the various salts to support the reaction of equation 2 so that it can compete with the reaction of equation 1. In view of the fact that the $(CH_3)_3P=CH_2$ compound gradually produced by the reaction of equation 1 undergoes in each particular case more rapid further reaction in accordance with equations 2 and 3, it is impossible for it to concentrate.

The present invention now provides, as a novel chemical compound, trimethyl phosphinimino dimethyl methylene phosphorane of the formula:

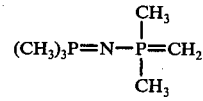

The invention also provides a process for making trimethyl phosphinimino dimethyl methylene phosphorane which comprises: reacting a tetramethyl phosphonium halide with 1.1 to 1.5 times the molar quantity of an alkali metal amide in an organic solvent, at temperatures of 0° to 35° C, with the exclusion of air and moisture, and over a period of 24 to 72 hours; removing the reaction mixture from residue and subjecting the reaction mixture to fractional distillation.

The solvents which are preferred in the above process comprise tetrahydrofurane, 1,2-dimethoxyethane or tetramethyl ethylene diamine.

It is also preferable for the reaction to be carried out at room temperature and for the reaction mixture to be intensively stirred during the reaction.

The formula II compound is a slightly yellow and highly reactive liquid which crystallizes well on cooling. Its composition and structure were identified analytically and spectroscopically. As it would appear from the $^1H$-, $^{13}C$- and $^{31}P$-spectra, the ylide is a fluctuating compound. At temperatures of about 80° C and more, all of its 17 hydrogen atoms as well as its 6 carbon atoms and 2 phosphorus atoms have been found to be equivalent to each other, NMR-spectroscopically. Only upon strong cooling down to about −20° to −80° C, is it possible for the different positions to be split spectroscopically. This phenomenon is the result of a rapid place exchange which occurs between the protons and which apart from intermolecular occurrences in the formula II compound, takes predominantly place intramolecularly between $CH_2$ and $CH_3$ groups of different phosphorus atoms.

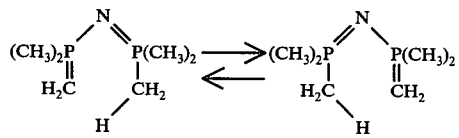

In the formula II ylide, the exchange of protons occurs substantially more rapidly than in the $(CH_3)_3P=CH_2$ compound.

The formula II compound finds widespread commercial uses. It may be reacted, for example, with an acid or ammonium salt thereof to give bis-trimethyl phosphoranylidene ammonium salts, which were difficult to prepare heretofore.

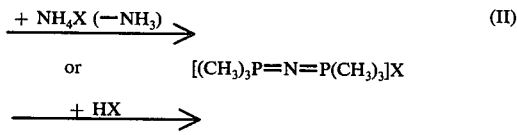

in which X stands for chlorine, bromine or iodine.

The formula II compound is also very well adapted for use as a complex former.

This is exemplified by the following equation, which is also applicable to bi- and further trivalent metals

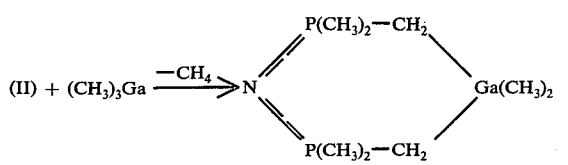

Alkali metal compounds can also be prepared. Last but not least, it is possible for the formula II compound to be used as ylide in a "Wittig reaction" for synthesizing organic compounds and even natural substances.

EXAMPLE 1

68 g (0.40 mol) of [(CH$_3$)$_4$P]Br was introduced into a suspension of 22 g (0.56 mol) of NaNH$_2$ in 750 ml of tetahydrofurane and the resulting reaction mixture was stirred for 35 hours at about 25° C with the exclusion of air and moisture. Residue, which was substantially NaBr, was filtered off and the filtrate was fractionated under vacuum. After the first runnings of (CH$_3$)$_3$P=CH$_2$, there was obtained 22.4 g (67.5% of the theoretical) of trimethyl phosphinimino dimethyl methylene phosphorane. The compound melted at 14° C and boiled at 148°–150° C under 30 mm Hg.

Elementary analysis: C$_6$H$_{17}$NP$_2$ (mol. wt: 165.2)
Calculated: C 43.62, H 10.38, N 8.48
Found: C 43.61, H 10.55, N 8.14

EXAMPLE 2

The procedure was the same as that described in Example 1 with the exception, however, that 50.6 g (0.4 mol) of [(CH$_3$)$_4$P]Cl was substituted for [(CH$_3$)$_4$P]Br. The same result as that in Example 1 was obtained.

We claim:

1. Trimethyl phosphinimino dimethyl methylene phosphorane of the formula:

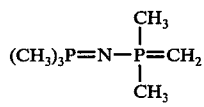

2. A process for making trimethyl phosphinimino dimethyl methylene phosphorane as claimed in claim 1, which comprises: reacting a tetramethyl phosphonium halide with 1.1 to 1.5 times the molar quantity of an alkali metal amide in an organic solvent, at temperatures of 0° to 35° C, with the exclusion of air and moisture, and over a period of 24 to 72 hours; removing the reaction mixture from residue and subjecting the reaction mixture to fractional distillation.

3. A process as claimed in claim 2, wherein the organic solvent is a member selected from the group consisting of tetrahydrofurane, 1,2-dimethoxyethane and tetramethyl ethylene diamine.

4. A process as claimed in claim 2, wherein the reaction is effected at room temperature and the reaction mixture is intensively stirred during the reaction.

* * * * *